(12) United States Patent
Metz-Stavenhagen

(10) Patent No.: US 6,214,006 B1
(45) Date of Patent: *Apr. 10, 2001

(54) APPARATUS FOR BRACING VERTEBRAE

(75) Inventor: Peter Metz-Stavenhagen, Bad Wildungen (DE)

(73) Assignee: Howmedica GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/454,582

(22) Filed: Dec. 7, 1999

Related U.S. Application Data

(62) Division of application No. 08/839,540, filed on Apr. 14, 1997, now Pat. No. 6,090,110, which is a continuation of application No. 08/384,639, filed on Feb. 6, 1995, now abandoned, which is a continuation of application No. 08/025,196, filed on Mar. 2, 1993, now abandoned.

(30) Foreign Application Priority Data

Mar. 2, 1992 (DE) .................................... 92 02 745

(51) Int. Cl.$^7$ ....................................................... A61F 2/00
(52) U.S. Cl. ................... 606/61; 606/60; 606/73
(58) Field of Search ................... 606/60, 61, 72, 606/73, 57; 623/17.11; 411/385, 393, 471, 920

(56) References Cited

U.S. PATENT DOCUMENTS

| 4,047,524 | * | 9/1977 | Hall | 606/61 |
| 4,383,438 | | 5/1983 | Eaton | 73/61.2 |
| 4,854,304 | * | 8/1989 | Zielke | 606/60 |
| 4,987,892 | * | 1/1991 | Krag et al. | 606/60 |
| 5,042,982 | * | 8/1991 | Harms et al. | 606/61 |
| 5,067,955 | | 11/1991 | Cotrel . | |
| 5,129,388 | * | 7/1992 | Vignaud et al. | 606/61 |
| 5,176,680 | * | 1/1993 | Vignaud et al. | 606/61 |
| 5,207,678 | * | 5/1993 | Harms et al. | 606/61 |

FOREIGN PATENT DOCUMENTS

| 2649042 | * | 1/1978 | (DE) | 606/60 |
| 0443892B1 | | 8/1991 | (EP) . | |
| 9101691 | | 2/1991 | (WO) . | |
| 9203100 | * | 5/1992 | (WO) | 606/61 |

* cited by examiner

*Primary Examiner*—Pedro Philogene
(74) *Attorney, Agent, or Firm*—Lerner, David, Littenberg, Krumholz & Mentlik, LLP

(57) ABSTRACT

An apparatus for bracing a plurality of vertebrae of the human spine has at least two pedicle screws, each having an annular head with an opening therewithin and including a slot therewithin. Each slot extends into the corresponding opening and includes internal threaded portions. A securing screw to be screwed in each slot is provided. A relatively stiff threaded rod is also provided and is to be inserted into the opening in the head of each of the pedicle screws and to be secured by the securing screws. Adjusting nuts are screwed on the rod and at least one cooperates with each head.

11 Claims, 3 Drawing Sheets

APPARATUS FOR BRACING VERTEBRAE

CROSS-REFERENCES TO RELATED APPLICATIONS

This application is a divisional of U.S. Ser. No. 08/839,540, filed Apr. 14, 1997 now U.S. Pat. No. 6,090,110 which is a continuation of U.S. Ser. No. 08/384,639, filed Feb. 6, 1995 now abandoned, which is a continuation of U.S. Ser. No. 08/025,196, filed Mar. 2, 1993 now abandoned.

The present invention relates to an apparatus for bracing a plurality of vertebrae of the human spine.

BACKGROUND OF THE INVENTION

1. Field of the Invention

Known supporting means operate with so-called lamina hooks which are disposed on a threaded rod. A compressing means is disclosed in British patent 2 131 300. A distracting means is disclosed in U.S. Pat. No. 4,383,438. The threaded rod bridges a plurality of vertebras and is not suited to act on vertebras which are disposed between the lamina hooks. The thread of the rod is used to fix the lamina hooks. Before using the supporting means a distraction or, respectively, compression has to be provided by means of an additional device.

DESCRIPTION OF THE PRIOR ART

German 90 06 646 U1 discloses an apparatus in which a lamina hook is replaced by a clamp-shaped holding member having a pair of legs of which one can be bent with respect to the other. Thereby the giapophysis of the vertebras may be used as anchoring points for the compressing and distracting apparatus.

German 88 02 112 U1 teaches a supporting device for the human spine, according to which the so-called pedicel screws are screwed in the pedicel body of the vertebras. The pedicle screws cooperate with tensioning means which bridge across one or more vertebrae to introduce forces between the vertebrae. The known device affords a primary stabilization of the vertebrae with respect to all degrees of freedom. However, when a number of vertebrae of a non-traumatic spine for example, are to be repositioned, separate means necessary to perform the reposition before the known supporting device may be effectively used.

WO 91/01691 discloses an apparatus for bracing vertebras of the human spine, comprising pedicle screws having slotted heads to receive a rod. The legs of the slotted screw heads include an outer thread on which a nut is screwed which contacts the rod to fix a predetermined position.

EP 0 443 892 discloses a similar device comprising a pedicle screw, the slotted head thereof including internal threaded portions for receiving a fixing screw which is brought into engagement with a serrated or similarly roughened rod to fix the relative position of the rod and the individual pedicel screw. A ring disposed around the head of a pedicle screw is provided so that the legs of the screw head do not spread apart while fixing the rod, as otherwise the engagement between the fixing screw and the screw head may be lost. A similar apparatus is disclosed in WO 90/09156.

Again, the devices last mentioned require separate means for repositioning, thus being suited to maintain a repositioned condition, but not suited to perform repositioning.

It is an object of the present invention to provide an apparatus which is suited to reposition the vertebrae of the human spine as well as to support the vertebrae in the repositioned position thereafter.

The objects are solved by the apparatus of the invention.

SUMMARY OF THE INVENTION

According to the invention, the apparatus uses a threaded rod (i.e., a distracting rod) in combination with lamina hooks. The thread of the rod, however, is not only used to fix the pedicle screws, but further is used to reposition the vertebrae in that an adjusting nut sitting on the threaded rod is turned with respect to the head of the pedicle screw and thus the vertebra has obtained the desired position. By means of the apparatus according to the invention a spine portion is not only distracted or compressed, but individual vertebrae can be effectively positioned with respect to each other. To this end the threaded rod is designed to be relatively stiff and has a diameter between 7 to 8 mm, for example. On the other hand the rod must be bent to be implanted close to the spine along a bent spine portion. This is facilitated by the design of the pedicle screw heads having slots for receiving the threaded rod. To hold the rod in the slot, a securing screw is provided. Whereas the screw in the pedicle screw head according to EP 0 443 892, for example, axially fixes the rod, the securing screw of the present invention is merely used to prevent a deflection of the rod out of the receiving slot.

After resetting, the adjusting nut must be fixed on the threaded rod. This can be obtained by means of a suitable counter-nut. Still further, it is possible, to provide the adjusting nut and the front faces of the pedicle screw head with a rotary safety means in form of a toothing or another irregularity cooperating in a clamping fashion. In both cases the nuts are merely fixed by a frictional force. According to a further embodiment of the invention, however, the head of the pedicle screw has a width smaller than the diameter of the securing screw, whereas at least one front face of the adjusting nut has a recess cooperating with the securing screw. Preferably, the adjusting nut includes a plurality of peripherally spaced indentations, wherein the final rotary position of the nut is such that the securing screw cooperates with the indentation. This affords a positive locking of the adjusting nut resulting in a precise rotary locking which cannot be loosened.

The pedicel screws must take up relatively large forces. There is the danger that a pedicel screw breaks out of the bone, primarily when the available bony substance does not provide a sufficiently rigid seat in the vertebra. According to an embodiment of the invention, a mounting strap is attached to the shaft of the pedicel screw laterally extending therefrom, which strap includes an opening for receiving a spongiose screw. The strap has, for example, a pair of openings, wherein one opening receives the shaft of the pedicel screw, while the other opening disposed at the other end of the strap, for example, receives a spongiose screw which is screwed into the vertebra. In this manner, the pedicel screw is laterally stabilized and can receive substantial forces. According to an alternate embodiment of the invention, a mounting strap may be provided to the shaft of the pedicel screw extending therefrom, which strap has a blade or the like to be mounted in the vertebra. The blade is preferably integral with the strap. The blade is beaten into the vertebra wherein the strap may additionally include a hole for receiving a spongiose screw which is screwed into the vertebra. In some cases, a vertebra is displaced with respect to the adjacent vertebra. When the pedicel screw is completely screwed in, it cannot be connected any more with the threaded rod. To accomplish a connection, the pedicel screw is partly screwed into the vertebra bone. According to an embodiment of the invention, the head of the pedicle screw is then rotatably mounted on the screw shaft so that by rotating the shaft the vertebra can be pulled up to the threaded rod for resetting. Preferably the shaft includes tool engaging faces adjacent the head to rotate the shaft of the screw in the desired manner.

In case of very specially displaced individual vertebrae, not even the features referred to above are suffient. According to a further embodiment of the invention, the upper end of the pedicle screw shaft is ball-shaped, while the pedicel screw head is defined by a ball-engaging cage including a slot for the rod. The cage can be arbitrarily positioned with respect to the shaft of the screw, but can exert a tensioning force to the screw shaft when being screwed in the vertebra. According to both embodiments just referred to, the threaded rod is inserted through a slot of the pedicel screw head, wherein a securing screw referred to several times prevents the rod from sliding out of the slot. Alternatively a closed passage may be provided in the head of the pedicle screw as it is known per se.

Instead of or in addition to the pedicle screw the apparatus of the present invention provides a hook cooperating with a lamina of a vertebra. Those lamina hooks are generally known. According to the invention, however, the lamina hook is provided with a slotted receiving portion to insert the threaded rod. The slot has threaded portions again to secure the rod in the receiving slot.

BRIEF DESCRIPTION OF THE DRAWINGS

Preferred embodiments of the invention will now be described by way of example with reference to the accompanying drawing.

BRIEF DESCRIPTION OF THE PREFERRED EMBODIMENTS

Figure 1:
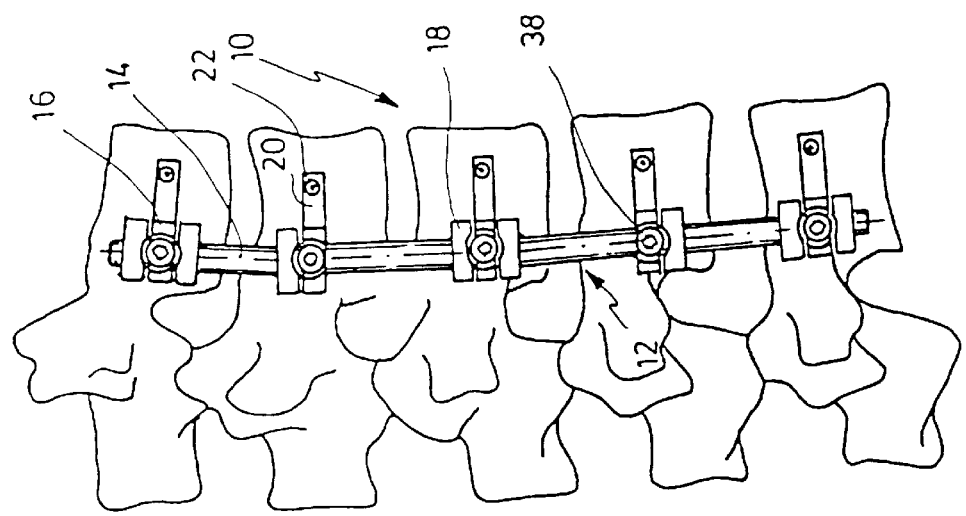
FIG. 1 schematically shows an apparatus according to the invention to be used as a distracting system, FIG. 2 schematically shows an apparatus according to the invention used as a compressing system.

FIG. 1 shows a bent spine portion 10 wherein the individual vertebras shall be distracted by means of a distracting system 12. The system comprises a relatively stiff threaded rod 14 having a diameter of 6 to 9 mm, preferably 7 to 8 mm. It cooperates with an individual pedicel screw 16 screwed in the vertebras. Details of the screws are shown in the following figures. The threaded rod 14 is received in slots of the pedicel screw heads 16 and a plurality of adjusting nuts 18 is disposed on the rod 14, at least one nut each for a pedicel screw 16. Stabilizing latches 20 cooperate with the pedicel screws, which latches include a hole 22 in a distance from the pedicle screw to receive a spongise screw screwed in the vertebra. By means of the adjusting nut 18 a pedicel screw screwed in the vertebra may be displaced relative to the rod 14 and thus with respect to the vertebra receiving the screw. By means of the adjusting nuts 18 the vertebrae of the portion 10 may be thus adjusted to accomplish a distraction.

Figure 2:
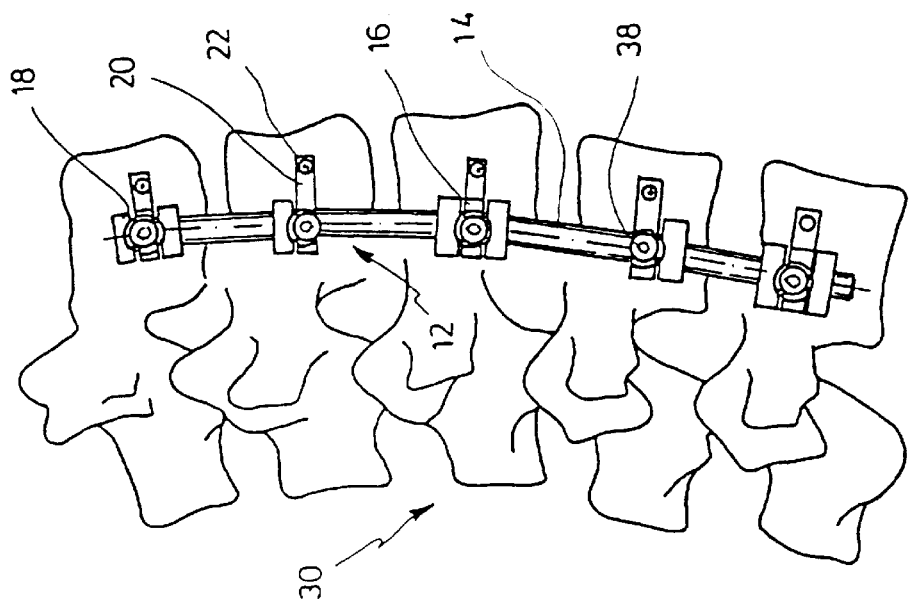

The spine portion 30 shown in FIG. 2 comprises a compressing means including components identical with those shown in the system 12 so that identical components carry identical reference numerals. To reduce the bending of the spine portion 30 a tension force must be exerted on the vertebras to straighten the bent threaded rod 14. This is accomplished by adjusting the individual pedic, screws 16 as described in FIG. 1. In the following the components of the system referred to are described in more detail.

Figure 3:
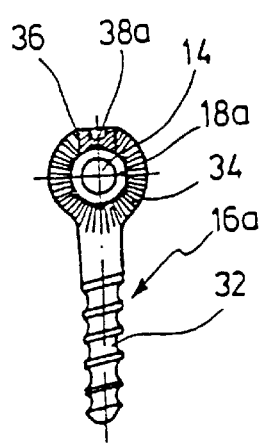
FIG. 3 shows a pedicel screw for the apparatuses according to FIGS. 1 and 2.
Figure 4:
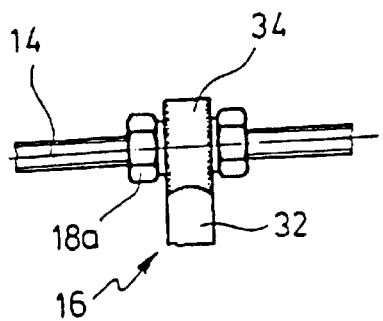
FIG. 4 shows the pedicel screw of FIG. 3 cooperating with a threaded rod, FIG. 5 schematically shows a side view of a further embodiment of a pedicel screw for the apparatuses of FIG. 1 and 2.

FIG. 3 shows a pedicel screw 16a having a shaft 32 and an annular head 34. The head 34 includes a slot 36 in which the rod 14 is inserted. A securing screw 38a cooperating with threaded portions in the slot 36 holds the threaded rod 14 in the slot 36. FIG. 4 shows adjusting nuts 18a located on either side of the head 34 to displace the screw 16a along the rod 14.

Figure 7:
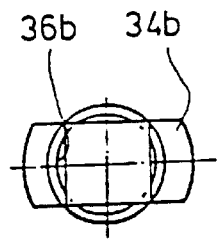
FIG. 7 shows a plain view of the pedicel screw of FIG. 5.
Figure 5:
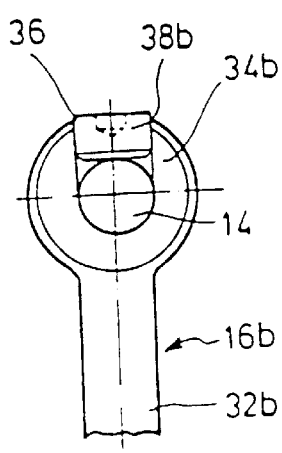
Figure 6:
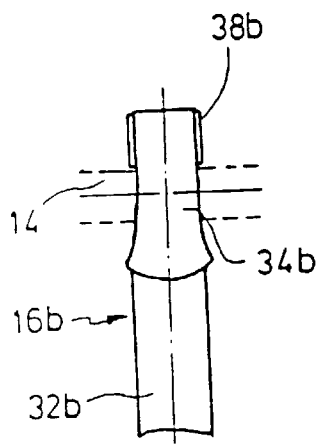
FIG. 6 shows a side view of the pedicel screw of FIG. 5 rotated about 90°.
Figure 8:
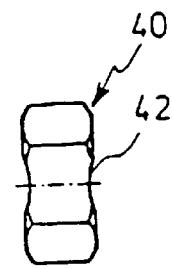
FIG. 8 shows a side view of an adjusting nut of the apparatus of FIGS. 1 and 2.

In the embodiment of FIGS. 5 and 6 the pedicel screw 16b has a relatively narrow head 34b so that the securing screw 38b laterally projects. This is shown by the dashed line in FIG. 7. when an adjusting nut 40 according to FIG. 8 is used, which nut is provided with indentations 42 on the opposite front faces thereof, the nut 40 can be secured to the rod 14 when an indentation 42 of the screw 38b cooperates with the adjusting nut 38b.

Figure 9:
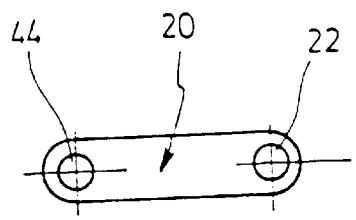
FIG. 9 shows a stabilizing strap for the apparatus of FIGS. 1 and 2.

FIG. 9 shows a mounting strap. The plate-shaped strap 20 includes a first hole 44 receiving the shaft of a pedidel screw. A second hole 22 receives a spongiose screw as mentioned before.

Figure 10A:
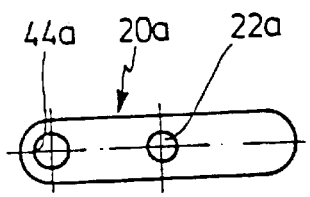
FIG. 10a shows a plan view of a further embodiment of a stabilizing strap of the apparatus of FIG. 1 and FIG. 2, including an integral blade.
Figure 10B:
FIG. 10b is an elevation view of the strap shown in FIG. 10a, FIG. 11 shows a section of a lamina hook for the apparatus of FIGS. 1 and 2.

FIG. 10 shows an alternate embodiment 20a of a stabilizing latch, again comprising a hole 44a for a pedicle screw and a hole 22a located substantially in the center for receiving a spongiose screw. FIG. 10 further shows a blade 46 integrally shaped on the end opposite the hole 44a which blade is driven home in the vertebra.

Figure 11:
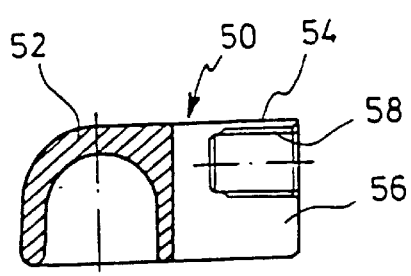
Figure 12:
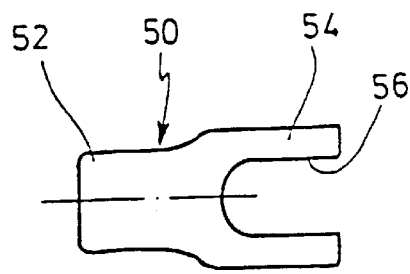
FIG. 12 shows a plain view of the hook of FIG. 11.

FIGS. 11 and 12 show a lamina hook 50 comprising a hook portion 52 and a receiving portion 54 including a slot 56.

The slot 56 receives a threaded rod such as the rod 14 shown in FIGS. 1 and 2. Threaded portions as indicated at 58 in FIG. 11 are provided inside the slot 56 to receive a securing screw not shown to hold the rod in the slot 56. The position of the rod in the slot 56 is determined by the position of the securing screw not shown, wherein a relative position between the hook 50 and the rod is possible to a limited extent.

Figure 13:
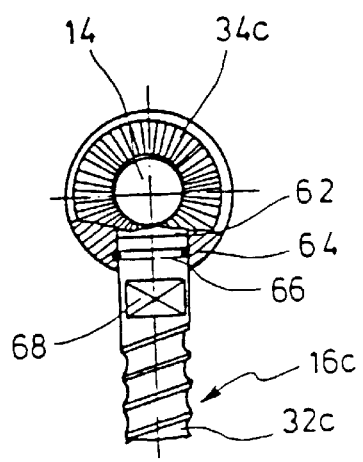
FIG. 13 shows a side view of a further embodiment of a pedicle screw for an apparatus according to the invention.
Figure 14:
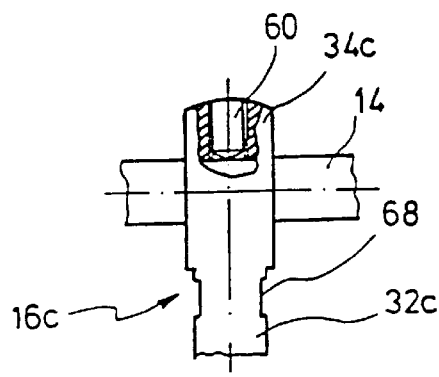
FIG. 14 shows a side view of the pedicle screw of FIG. 13 turned about 90°.

FIGS. 13 and 14 show a pedicel screw 16c comprising a shaft 32c and an annularly closed head 34b through which a rod 14 extends. A fixing screw 60 in the head 34b is used to fix the threaded rod 14. However, adjusting nuts may be used as mentioned before. According to the embodiment of FIGS. 13, 14 the shaft 32c is rotatably mounted in the head 34b. Accordingly, a circular blind bore 62 holds a ring 64 cooperating with an annular groove 66 in the shaft 32. Tool faces 68 facilitate a rotation of the shaft 32c relative to the head 34c when it fixedly sits on the rod 14 for example. It should be understood that the head 34c may provide a slot as shown in FIGS. 3 to 7 for example.

Figure 15:
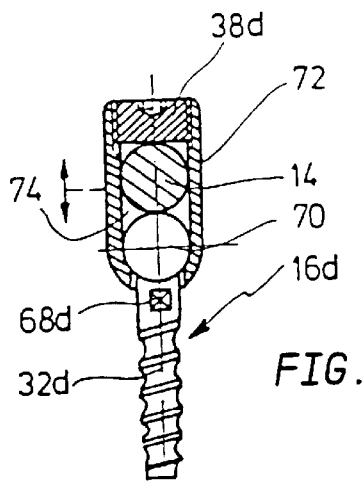
FIG. 15 shows a side view partly in section of a further embodiment of a pedicle screw for an apparatus according to the invention and FIG. 16 shows a side view of the pedicle screw of FIG. 15 turned around 90°.
Figure 16:
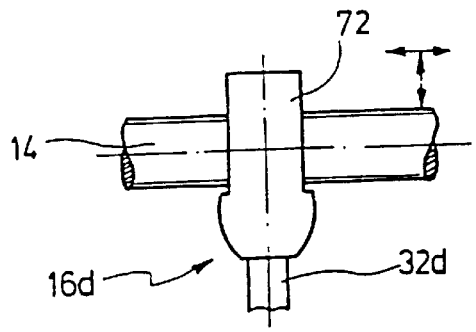

In the embodiment of FIGS. 15 and 16 a pedicel screw 16d is provided comprising a shaft 32d which upper end is formed as a ball 50. A cage 72 cooperates with the ball, the cage further having a passage 74 to receive a threaded rod 14. Furthermore, the cage 72 has threaded portions to receive a securing screw 38c. This allows to rotate the shaft 32, wherein tool faces 68d are provided. Furthermore, the shaft 32d may be pivoted relative to the cage 72 in a limited angle.

What is claimed is:

1. An apparatus for bracing a plurality of vertebrae of the human spine, comprising: at least two pedicle screws having a shaft and a head including a slot which extends into the head and includes internal thread portions, a securing screw to be screwed in said slot on said thread portions, a threaded rod to be inserted into the slot in the head of the pedicle screws and secured by said securing screws, and adjusting nuts screwed on said rod and cooperating with said head wherein the head of the pedicle screw has a pair of faces in the area of said slot defining a width therebetween smaller than a diameter of the securing screw so that a portion of the screw extends beyond the head faces and wherein the adjusting nut has a recess provided on the face thereof adjacent the head face for cooperating with said securing screw portion to prevent the rotation of the nut after the securing screw is threaded into said slot.

2. The apparatus of claim 1, wherein the threaded rod has a diameter of between 6 to 9 mm.

3. The apparatus of claim 1, wherein a laterally extending mounting latch may be attached to the shaft of the pedicel screw which latch has an opening to receive a spongiose screw.

4. The apparatus of claim 1, wherein a laterally extending mounting strap is attached to the shaft of the pedicel screw which strap has a blade to be mounted in the vertebra.

5. The apparatus of claim 4, therein the blade is integrally formed on the strap preferably at the free end thereof.

6. The apparatus of claim 1, wherein the head of the pedicle screw is rotatably mounted on the shaft.

7. The apparatus of claim 6, wherein an upper end of the shaft of the pedicle screw is shaped as a ball and wherein the head of the pedicle screw is formed by a cage receiving said ball including the slot for the threaded rod.

8. The apparatus of claim 7, wherein a lamina hook is provided comprising a slotted receiving portion for the threaded rod and comprising threaded portions in the receiving slot portion to receive a securing screw fixing the threaded rod in the slot.

9. A pedicle screw assembly comprising:

a pedicle screw having a shaft and a head with a U-shaped opening therethrough with an internal thread extending along said U-shaped opening towards said shaft;

a threaded rod for insertion into and between the U-shaped opening of the pedicle screw;

a securing screw threaded into said U-shaped opening on said internal thread for moving said rod toward said shaft, said screw having a diameter greater than a thickness of said head so as to have a portion extending outwardly of said head; and at least one nut disposed about the rod and making contact with said pedicle screw head, said nut including at least one indentation about a face thereof facing said head for engaging said outwardly extending portion of said securing screw upon the insertion of the screw into said U-shaped opening to prevent the rotation of said nut.

10. The apparatus of claim 9 wherein the head of the pedicle screw is rotatably mounted on the shaft.

11. The apparatus of claim 9 wherein an upper end of the shaft of the pedicle screw is shaped as a ball and wherein the head of the pedicle screw is formed by a cage receiving said ball including the slot for the threaded rod.

* * * * *

UNITED STATES PATENT AND TRADEMARK OFFICE
CERTIFICATE OF CORRECTION

PATENT NO. : 6,214,006 B1  
DATED : April 10, 2001  
INVENTOR(S) : Metz-Stavenhagen Page 1 of 1

It is certified that error appears in the above-identified patent and that said Letters Patent is hereby corrected as shown below:

Column 1,
Lines 36, 37, 56, "pedicel" should read -- pedicle --.

Column 2,
Lines 45, 46, 50, 54, 57, 60, 66, "pedicel" should read -- pedicle --.

Column 3,
Lines 2, 12, 18, "pedicel" should read -- pedicle --.
Line 23, after "of" insert -- , --.
Line 23, after "to" insert -- , --.
Line 23, after "screw" insert -- , --.
Lines 40, 42, 45, 48, 50, "pedicel" should read -- pedicle --.

Column 4,
Lines 14, 17, 18, 19, 22, 36, 43, 53, "pedicel" should read -- pedicle --.
Line 33, "pedic," should read -- pedicle --.

Column 5,
Lines 6 and 18, "pedicel" should read -- pedicle --.

Column 6,
Lines 2 and 6, "pedicel" should read -- pedicle --.

Signed and Sealed this

Thirteenth Day of November, 2001

Attest:

NICHOLAS P. GODICI
*Attesting Officer*    *Acting Director of the United States Patent and Trademark Office*